US012611158B2

(12) United States Patent     (10) Patent No.:   US 12,611,158 B2

Gao et al.     (45) Date of Patent:    Apr. 28, 2026

---

(54) DETENT PROCESS FOR MEDICAL IMAGING SYSTEMS

(71) Applicant: KONINKLIJKE PHILIPS N.V., Eindhoven (NL)

(72) Inventors: Xiang Gao, Suzhou (CN); Gang Yang, Suzhou (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 94 days.

(21) Appl. No.: 18/693,245

(22) PCT Filed: Sep. 6, 2022

(86) PCT No.: PCT/EP2022/074716
§ 371 (c)(1),
(2) Date: Mar. 19, 2024

(87) PCT Pub. No.: WO2023/046460
PCT Pub. Date: Mar. 30, 2023

(65) Prior Publication Data
US 2025/0241610 A1    Jul. 31, 2025

(30) Foreign Application Priority Data

Sep. 23, 2021   (WO) ................ PCT/CN2021/119795
Dec. 7, 2021   (EP) ..................................... 21212726

(51) Int. Cl.
*A61B 6/00*      (2024.01)
*A61B 6/10*      (2006.01)
*A61B 6/58*      (2024.01)

(52) U.S. Cl.
CPC .............. *A61B 6/547* (2013.01); *A61B 6/105* (2013.01); *A61B 6/4476* (2013.01); *A61B 6/582* (2013.01);

(Continued)

(58) Field of Classification Search
CPC ......... A61B 6/105; A61B 6/44; A61B 6/4452; A61B 6/4464; A61B 6/4476; A61B 6/547; A61B 6/582
See application file for complete search history.

(56) References Cited

U.S. PATENT DOCUMENTS 6,459,226 B1   10/2002   Zettel
2006/0083353 A1   4/2006   Boomgaarden
(Continued)

FOREIGN PATENT DOCUMENTS

EP      1157661 A2   11/2001
EP      1157661 A3   6/2003
WO   WO2020259794 A1   12/2020

OTHER PUBLICATIONS

PCT International Search Report, International application No. PCT/EP2022/074716, Dec. 9, 2022.

*Primary Examiner* — Mark R Gaworecki
(74) *Attorney, Agent, or Firm* — Larry Liberchuk

(57) ABSTRACT

A detent method for a medical imaging system. The method comprises obtaining a braking function F(S, V) between a distance S moved by a moveable component of the medical imaging system when a brake is applied to the component and a velocity V of the component and obtaining a measured velocity $V_m$ of the component before the brake is applied. A braking position $P_B$ is determined based on a target position $P_T$, the measured velocity $V_m$ and the braking function F(S, V), wherein the brake is configured to be actuated when the component reaches the braking position $P_B$.

14 Claims, 4 Drawing Sheets

(52) U.S. Cl.

CPC ............... *A61B 6/44* (2013.01); *A61B 6/4452*
(2013.01); *A61B 6/4464* (2013.01)

(56)                    References Cited

U.S. PATENT DOCUMENTS

2007/0121791  A1      5/2007  Haupl
2015/0043716  A1      2/2015  Lee

DETENT PROCESS FOR MEDICAL IMAGING SYSTEMS

FIELD OF THE INVENTION

The invention relates to the field of detent processes for medical imaging systems.

BACKGROUND OF THE INVENTION

Conventional digital X-ray (DXR) Ceiling Suspension (CS) systems and tubestand subsystems use a mechanical method or an electrical brake to perform an auto-detent process. Most of the DXR systems use mechanical methods due to the existence of many different detent mechanical structures and their use on industrial products with a long history.

For a DXR system, there are two normal system structures. Wallstand and table systems are used to support a subject and an X-ray detector. CS and tubestand subsystems are used to support an X-ray source (tube). The distance between the source and detector impacts the quality of the X-ray image. There are some values of distances which are used often (e.g. 110 cm, 150 cm and 180 cm).

When using the mechanical method, mechanical parts (e.g. limit pins and limit holes) are activated to stop the systems at a target position. A few systems use an electrical brake method. When using the electrical brake method, an electric brake is activated when the CS/tubestand reaches a target position and the CS/tubestand stops after it slides an accepted distance. However, both the mechanical method and electrical brake method have disadvantages.

Mechanical methods may be relatively accurate and precise. However, the mechanical method requires the installation of additional parts (e.g. limit pins and limit holes). This make the CS/tubestand subsystem mechanical structure more complex. Additionally, the additional parts may increase the cost and installation time of the systems. The kinetic energy of the system may also be mostly cancelled out by vibration in the system, which may make a user uncomfortable.

Electrical brake methods do not require the additional mechanical parts, but they also have disadvantages. The detent position precision has a relatively large error when the mass of the subsystem is relatively large or when the velocity (before enabling the brake) is relatively large. Particular brake forces may need a larger braking distance to cancel out the kinetic energy. However, most CS/tubestand subsystems (especially in high performance systems) are heavy. Secondly, the brake needs to activated ahead of time as the CS system approaches the target position, and it is difficult to determine the suitable braking time. The braking force may also change with friction surface conditions or a change in the braking gap.

In addition, sometimes the braking forces are applied manually by operators, therefore, the value of the forces is hard to predict and varies by operators.

EP1157661 introduced a detent control system for reducing position errors in the positioning of an X-Ray tube including how to calculate overshoot correction. However, the article fails to consider some factors, like errors caused by operators, also it does not give the effectiveness evaluation of the correction, or the re-calibration/adjustment condition for the correction during a braking operation process. Thus, there is a need for an improved detent process.

SUMMARY OF THE INVENTION

The invention is defined by the claims.

According to examples in accordance with an aspect of the invention, there is provided a detent method for a medical imaging system, the method comprising:

obtaining a braking function F(S, V) between a distance S moved by a moveable component of the medical imaging system when a brake is applied to the component and a velocity V of the component;

obtaining a measured velocity $V_m$ of the component before the brake is applied; and determining a braking position $P_B$ based on a target position $P_T$, the measured velocity $V_m$ and the braking function F(S, V), wherein the brake is configured to be actuated when the component reaches the braking position $P_B$.

The distance S moved by a moveable component of the medical imaging system when a brake is applied to the component may be defined as the difference between the braking position $P_B$ and the target position $P_T$, such that $S=|P_T-P_B|$.

Using a braking function to determine a braking position enables the detent method to stop the component at (or at least near) the target position. The braking position defines the position at which the brake needs to be applied to the component in order to make the component stop at the target position. The method may further comprise:

obtaining a measured position $P_m$ of the component after the component stops moving; and if the measured position $P_m$ does not fall within a detent window relative to the target position $P_T$, adjusting the braking function F(S, V) based on:

a distance $S_0$ between the braking position $P_B$ and the measured position $P_m$; and the measured velocity $V_m$.

In this way, the method is, in essence, an auto-calibration method for an automatic detent process. The detent process enables the component to be positioned at particular pre-determined target positions on, for example, a railing system. The calibration (i.e. adjusting the braking function) ensures the component stops within a particular "detent window" (e.g. within +1 cm) from the pre-determined target position. If the component stops outside the detent window, then the latest movement data (i.e. the distance moved by the component and the velocity before braking begins) is used to re-calibrate the detent process.

The detent process is based on a braking function which defines how far the component moves when a brake is applied to the component relative to the velocity at which it was travelling when the brake is applied. This function may change over time (e.g. wear of the braking system) or based on outside parameters (e.g. temperature).

Thus, the inventors propose checking the function is performing correctly (i.e. the measured position similar to the target position) after a movement of the component and, if it is not performing correctly, adjusting the braking function based on the latest movement data.

The method does not require additional complex mechanical parts on the component which may wear over time and need to be installed on the component (and/or on a system associated with the movement of component). Additionally, mechanical detent processes usually generate vibrations on the component due to the sudden change in kinetic energy of the component.

Additionally, the method does not have a higher error when the measured velocity (before braking) is relatively high nor when the mass of the component is high, as often occurs with electronic detent processes.

The component is a moveable component. The component may be a moveable medical component such a DXR ceiling suspension subsystem or a tubestand subsystem.

The braking function F(S, V) may be a quadratic function where $S \propto V^2$. The inventors realized that the braking function can be approximated to a quadratic function based on the conservation of energy. The kinetic energy of the component is equal to $\frac{1}{2}mV^2$, where m is the mass of the component and V is the velocity of the component. The energy absorbed by the brake is approximately $f_T S$, where $f_T$ is the total force acting on the component (e.g. including the braking force, forces due to friction and an operating force on the component) and S is the distance travelled by the component during braking.

The operating force may be manually applied by an operator (i.e. an operator moving the component). The value of the operating force is significantly harder to predict than some of the other forces. This is due to the behavior of operators being difficult to predict. For example, if the behavior of an operator varies significantly to the behavior of the worker who initially calibrated the breaking function, the breaking function may no longer be able to assure accuracy. Thus, it may be advantageous to adjust the breaking function after one or more movements of the component. This ensures that the breaking function gets used to particular behaviors of an operator.

The braking function F(S, V) may be a quadratic function $S=KV^2$ between the distance moved by the component, S, and the velocity of the component, V, wherein K is a calibration constant and wherein adjusting the braking function $S=KV^2$ comprises adjusting the value of the calibration constant K.

The braking function may be defined as $$S = \frac{m}{2F_T} V^2$$

if it is assumed that no other terms are relevant in the conservation of energy equation. The total force and the mass can be assumed to be constant and, thus, the braking function can be defined as a quadratic equation with one constant $$K = \frac{m}{2F_T}.$$

The constant K may be estimated based on estimated values of m and $F_T$. Alternatively, the constant may be calculated based on measured values of S and V.

Using the equation $S=KV^2$ enables the braking function to be a linear relationship between S and $V^2$. Thus, only two known pairs of values for S and $V^2$ are needed to determine a calibrated value for K. One of these pairs may be S=0 and $V^2$=0.

The braking function F(S, V) may be a quadratic function, $S=aV^2+bV+c$, between the distance moved by the component, S, and the velocity of the component, V, wherein a, b and c are calibration constants and wherein adjusting the braking function $S=aV^2+bV+c$ comprises adjusting the values of one or more of the calibration constants a, b and c.

It may be beneficial to also consider other factors affecting the braking function. For example, there may be a time delay between the initiation of braking and the time at which the component begins braking. This would mean $$\text{the braking function would be} = \frac{m}{2F_T} V^2 + \Delta t V,$$

where $\Delta t$ is the time delay between the initiation of braking and the component beginning to brake and can be approximated as being constant.

Additionally, the measured velocity may not be precise or the velocity sensor used to measure the velocity may have a bias. Thus, $$\text{the braking function would be} = \frac{m}{2F_T} (V + \Delta V)^2,$$

where $\Delta V$ is a bias or error in the velocity measurement and can be approximated as being constant.

Thus, the inventors realized that the braking function may be better approximated as the general quadratic function $S=aV^2+bV+c$.

Determining a braking position $P_B$ may comprise determining a braking distance $S_B$ based on applying the measured velocity $V_m$ to the braking function F(S, V) and determining the braking position $P_B$ based on the difference between the target position $P_T$ and the braking distance $S_B$.

Obtaining the braking relationship F(S, V) may comprise obtaining at least two measured distances $S_m$ travelled by the component when the brake is actuated, obtaining at least two measured velocities $V_m$ corresponding to the velocity of the component when braking begins for the at least two measured distances $S_m$ respectively and fitting a function F(S, V) for the at least two pairs $[S_m, V_m]$.

The invention also provides a computer program product comprising computer program code which, when executed on a computing device having a processing system, cause the processing system to perform all of the steps of the detent method.

The invention also provides a system for performing a detent method for a medical imaging system, the system comprising a processor configured to:

obtain a braking function F(S, V) between a distance S moved by a moveable component of the medical imaging system when a brake is applied to the component and a velocity V of the component;

obtain a measured velocity $V_m$ of the component before the brake is applied; and determine a braking position $P_B$ based on a target position $P_T$, the measured velocity $V_m$ and the braking function F(S, V), wherein the brake is configured to be actuated when the component reaches the braking position $P_B$.

The processor may be further configured to obtain a measured position $P_m$ of the component after the component stops moving and, if the measured position $P_m$ does not fall within a detent window relative to the target position $P_T$, adjust the braking function F(S, V) based on a distance $S_0$ between the braking position $P_B$ and the measured position $P_m$ and the measured velocity $V_m$.

The braking function F(S, V) may be a quadratic function where $S \propto V^2$. For example, the braking function F(S, V) may be a quadratic function $S=KV^2$ between the distance moved by the component, S, and the velocity of the component, V, wherein K is a calibration constant and wherein the processor is configured to adjust the braking function $S=KV^2$ by adjusting the value of the calibration constant K.

The braking function $F(S, V)$ may be a quadratic function, $S=aV^2+bV+c$, between the distance moved by the component, S, and the velocity of the component, V, wherein a, b and c are calibration constants and wherein the processor is configured to adjust the braking function $S=aV^2+bV+c$ by adjusting the values of one or more of the calibration constants a, b and c.

The system may comprise one or more positioning rails, with the component placed on the positioning rails, a movement system configured to move the component along the positioning rails and a braking system configured to stop the component from moving.

The system may further comprise one or more of a position sensor configured to obtain the measured position $P_m$ of the component and a velocity sensor configured to determine the measured velocity $V_m$ of the component.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figures 1, 2:
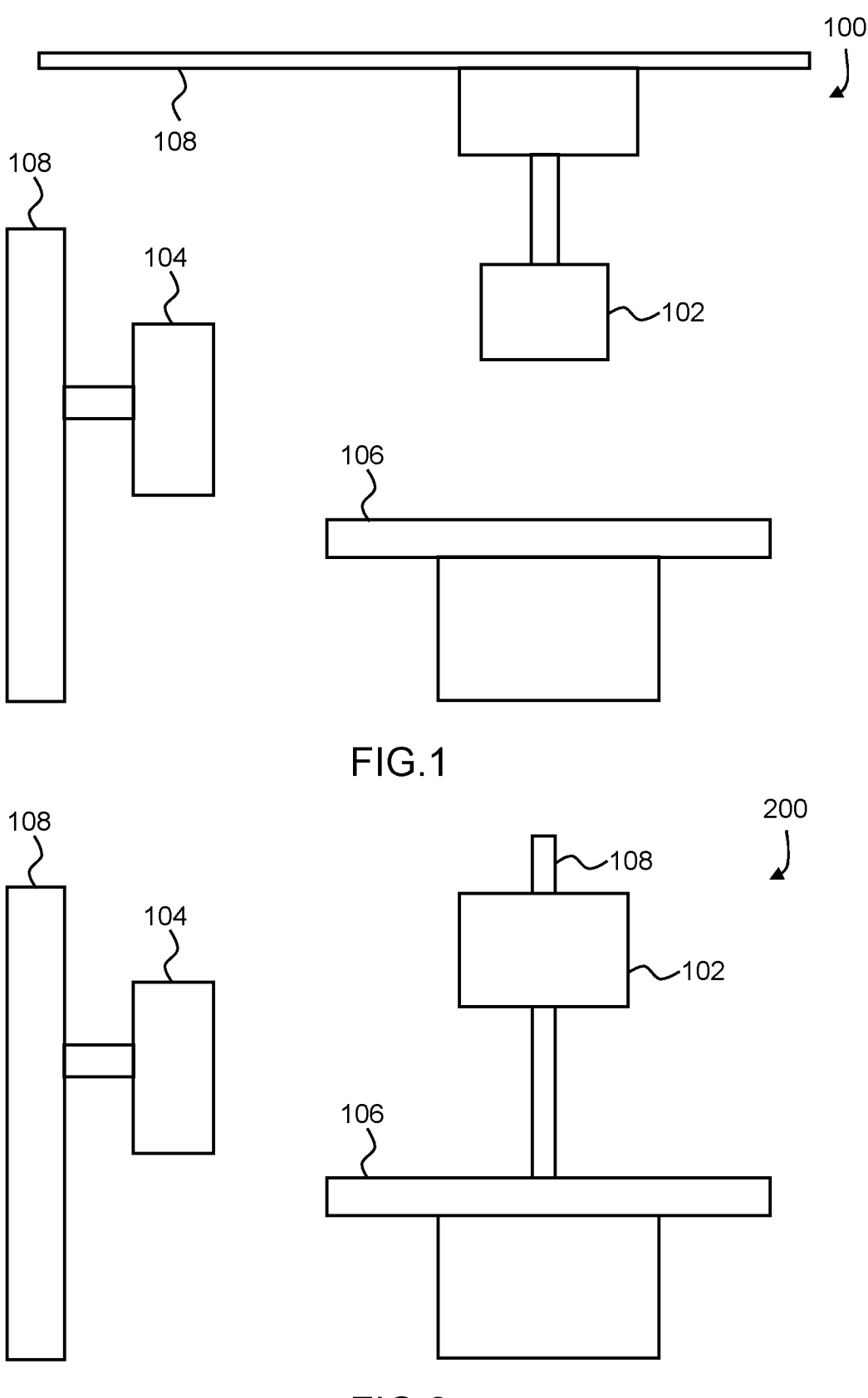
FIG. 1 shows an illustration of a conventional DXR ceiling suspension system.
FIG. 2 shows an illustration of a conventional tubestand system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a detent method for a medical imaging system. The method comprises obtaining a braking function $F(S, V)$ between a distance S moved by a moveable component of the medical imaging system when a brake is applied to the component and a velocity V of the component and obtaining a measured velocity $V_m$ of the component before the brake is applied. A braking position $P_B$ is determined based on a target position $P_T$, the measured velocity $V_m$ and the braking function $F(S, V)$, wherein the brake is configured to be actuated when the component reaches the braking position $P_B$.

System:

FIG. 1 shows an illustration of a conventional DXR ceiling suspension (CS) system 100. The CS system 100 is one example of a possible medical imaging system to which the invention may be applied. The CS system 100 comprises a scanner 102 suspended from the ceiling and movable via rails 108. The CS system 100 also comprises a wallstand 104 movable via rails 108 and a table 106. The table may also be movable. The current invention may be used to move the scanner 102, the wallstand 104 and/or the table 106.

FIG. 2 shows an illustration of a conventional tubestand system 200. The tubestand system 200 is another example of a possible medical imaging system to which the invention may be applied. The tubestand system 200 comprises a scanner 102 which may be moved vertically via rails 108. The scanner 102 may also be configured to move horizontally via additional rails on the floor. The tubestand system 200 also comprises a wallstand 104 movable via rails 108 and a table 106. The table may also be movable. The current invention may be used to move the scanner 102, the wallstand 104 and/or the table 106.

Other medical imaging systems (e.g. X-ray scanners, ultrasound scanners, CT scanners etc.) which comprise moving components may also be used.

Figure 3:
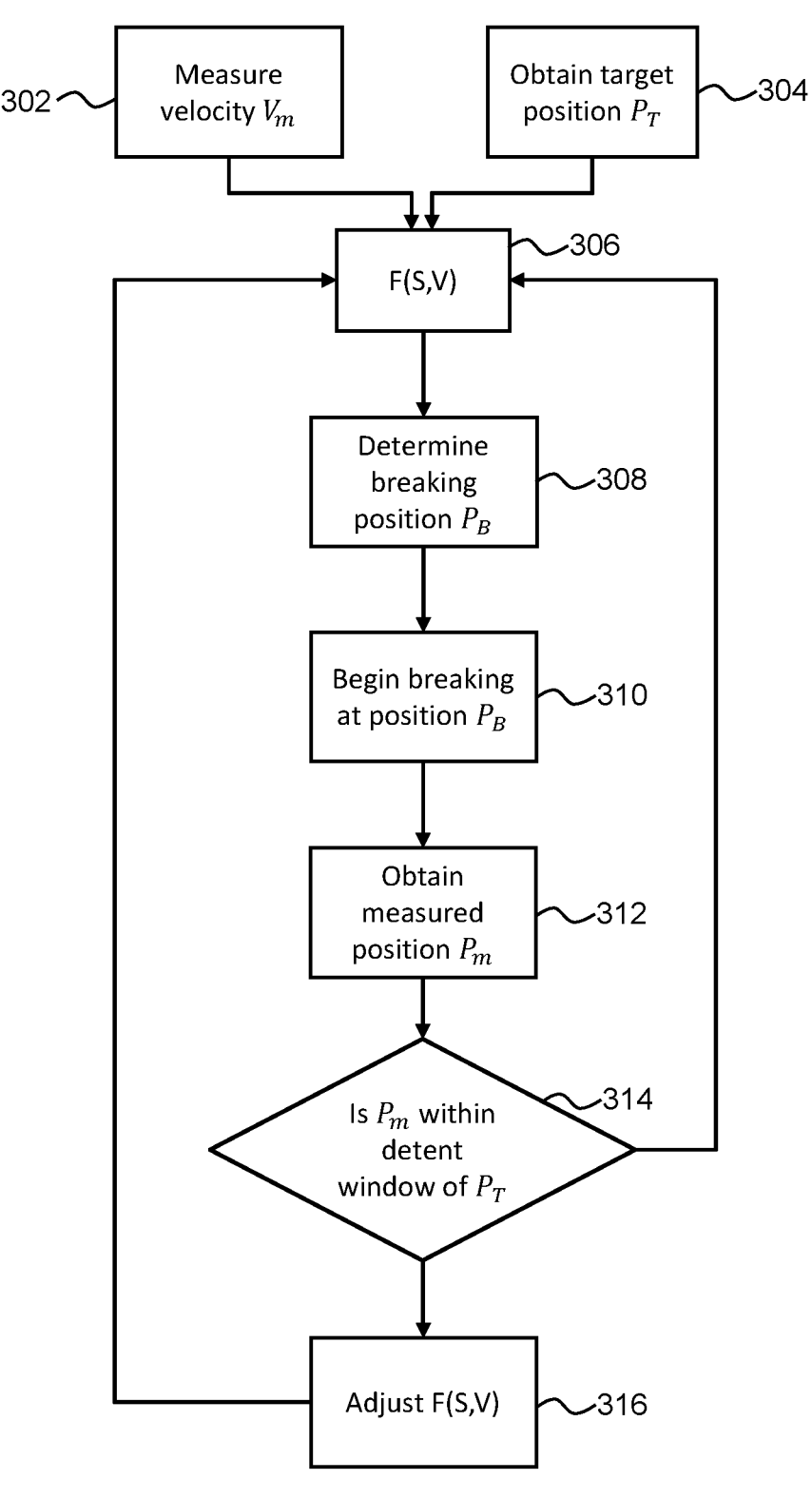
FIG. 3 shows a flow chart for a detent method according to the claims.

FIG. 3 shows a flow chart for a detent method according to the claims. During factory debugging or during field installation debugging, a calibration may be performed to derive an initial relationship $F(S, V)$ between a brake distance S and the measured velocity $V_m$ before enabling a brake.

An algorithm (according to the flow chart) will, in real-time, determine in step 302 the measured velocity $V_m$ of a moveable component based on, for example, the data of position sensor (e.g. a potential meter or absolute encoder) or a velocity sensor. A target position $P_T$ is also obtained in step 304 defining where the user wants the component to stop (i.e. a detent position). The velocity $V_m$ is input in step 306 into the initial relationship $F(S, V)$ to calculate the needed brake distance $S_0$ and thus the braking position $P_B$ can be determined in step 308 based on the difference between the brake distance S and the target position $P_T$.

Once the component is detected to be at the braking position $P_B$, the brake is enabled 310 to make the component stop. The component will naturally decelerate to zero due to the brake and should stop at the target position $P_T$.

The position $P_m$ at which the component actually stops may also be measured in step 312. If the measured position $P_m$ is outside a pre-defined detent window (e.g. ±1 cm) 314, the braking function $F(S, V)$ may need to be adjusted in step 316 based on the measured velocity $V_m$ and the braking distance S between the braking position $P_B$ and the measured position $P_m$.

Adjusting the braking function $F(S, V)$ in step 316 may preferably be based on one or more rules to trigger re-calibration (e.g. two continuous failures to stop within the detent window). In some cases, a particular movement of the component may be accidental or particularly different to common behaviors for manually moving the component (e.g. an operator losing control of the movement). Thus, triggering the re-calibration step (i.e. box 316) may comprise a more complex set of rules to avoid adjusting the breaking function $F(S, V)$ based on accidental data. One particular rule may be to only adjust the breaking function F(S, V) after two consecutive movements which fall outside the pre-defined detent window.

Adjusting 316 the braking function F(S, V) is, in essence, a re-calibration of the braking function F(S, V). If the algorithm performs the afore-mentioned checks for each movement of the component, the algorithm is, in essence, an automatic re-calibrating algorithm which maintains detent precision.

Braking Function:

It will now be explained how the form of a braking function may be obtained. Firstly, the following set of variables will be defined (with example values for a tube-stand system 200 as shown in FIG. 2):

S—The braking distance;
$V_m$—The measured velocity (e.g. 25 cm/s);
$f_B$—Braking force (e.g. 270 N);
M—Mass of the component (e.g. 390 kg);
$f_f$—Friction force (e.g. 40 N);
$f_O$—Operating force; and
t—The time from enabling brake to the component stopping.

An initial equation can be obtained based on the conservation of energy by equating the kinetic energy of the component to the energy of the forces applied to the component:

$$S = \frac{m}{2(f_B + f_f - f_O)} V_m^2$$

The initial equation can be modified by considering the time delay $\Delta t$ between the brake being enabled and the braking action beginning:

$$S = \frac{m}{2(f_B + f_f - f_O)} V_m^2 + \Delta t V_m$$

The initial equation can also be modified by considering that the braking force $f_B$ needs time to stabilize and reach a maximum value. Thus, the braking force $f_B$ can be modified to an average braking force $\overline{f_B}$:

$$S = \frac{m}{2(\overline{f_B} + f_f - f_O)} V_m^2$$

Where $\overline{f_B} < f_B$.

The user may also change the operating force frequently. The operating force is a manually exerted force by a user and is typically unpredictable. In general, the operating force may vary based on the particular user, the physical condition of the user (e.g. injuries etc.) or even on the time of day (e.g. user may be tired at the end of the day and apply less force).

Thus, the operating force $f_O$ can be modified in the initial equation to an average operating force $\overline{f_O}$:

$$S = \frac{m}{2(f_B + f_f - \overline{f_O})} V_m^2$$

Where $\overline{f_O} > f_O$ or $\overline{f_O} < f_O$.

Similarly, the friction force may also be different at different positions. Thus, the braking force $f_f$ can be modified to an average braking force $\overline{f_f}$:

$$S = \frac{m}{2(f_B + \overline{f_f} - f_O)} V_m^2$$

Where $\overline{f_f} > f_f$ or $\overline{f_f} < f_f$.

Additionally, the measured velocity may not be fully accurate and thus a velocity error (or velocity bias) $\Delta V_m$ may be considered such that the initial equation is modified to:

$$S = \frac{m}{2(f_B + f_f - f_O)} (V_m + \Delta V_m)^2$$

Thus, by considering all of the above possible modifications to the initial equation, a modified equation may be constructed such that:

$$S = \frac{m}{2 f_T} (V_m + \Delta V_m)^2 + \Delta t V_m$$

Where $f_T$ is the total sum of all the (average) forces applied to the component. Clearly this is a quadratic equation. The braking distance S can be defined as the distance between the target position $P_T$ and the braking position $P_B$. Thus, a general equation may be constructed:

$$P_B - P_T = a V_m^2 + b V_m + c$$

Where a, b and c are constants based on the modified equation above.

Figure 4:
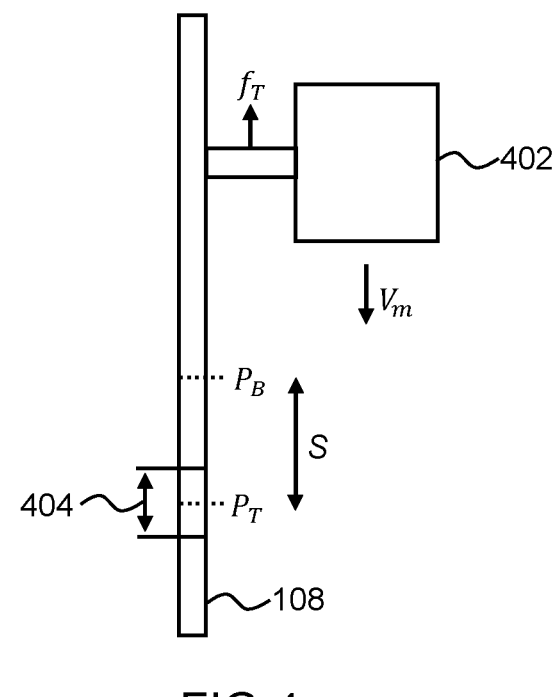
FIG. 4 shows a component moving at a velocity I'm on a rail.

FIG. 4 shows a component 402 moving at a velocity $V_m$ on a rail 108. The target position $P_T$ and the corresponding braking position $P_B$ are shown. A detent window 404 is also shown. A user will push a button to disable the brake and manually move the component 402 to a pre-defined position (i.e. the target position $P_T$). An algorithm will then actuate the brake at the braking position $P_B$ and record the measured position $P_m$ at which the component 402 stops. If the component 402 stops within the detent window 404, then there may be no need to re-calibrate the braking function (e.g. adjusting the constant a, b and c in the general equation above). However, if the component 402 does not stop within the detent window 404, the constants of equation may need to be adjusted/re-calibrated to improve the accuracy/precision of the equation. The re-calibration may be based on a set of rules (e.g. two consecutive movements falling outside of detent window, time-period between two consecutive movements less than a pre-determined time e.g. one hour etc.).

The movement is likely begun by an operating force. The operating force may or may not continue to be applied when the break is engaged based on many different factors. One of the most significant factors is the particular behaviors/habits of different users (i.e. operators).

Some operators may continue to apply the operating force until the component 402 has completely stopped. This kind of behavior is typical of users who are confident in the accuracy of the detent. Other operators may stop applying the force as soon as the break is first applied, which will reduce the average operating force. The operating force is usually small relative to the mass of the component 402. However, due to the variations in the operating force, the breaking function may have to be adjusted (i.e. re-calibrated) whenever a different operator is using the system.

The component 402 in FIG. 4 is shown as moving vertically. However, it will be appreciated that the component 402 could be moving horizontally (or even at an angle, if required). When moving vertically, a constant breaking force may be applied to the component 402 to counteract the force due to gravity.

Figure 5:
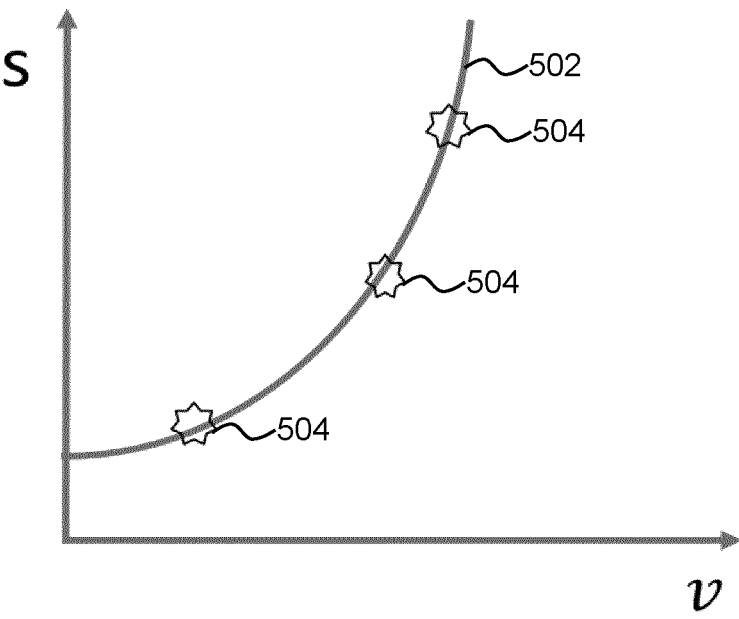
FIG. 5 shows a quadratic curve which may be used to find the braking function.

FIG. 5 shows a quadratic curve 502 which may be used to find the braking function. In order to initially calibrate the braking function, the brake may be activated at a target position $P_T$. The corresponding velocity $V_m$ and the distance $S_m$ from the target position $P_T$ at which the component stops could then be measured. This is then repeated at least three times for three different velocities. The three calibration measurement 504 can then be plotted and fitted to a quadratic curve 502 in order to obtain the constants a, b and c. In some cases, the constants b and/or c may be assumed to be negligible and thus only two (or even one) measurements may be necessary.

Figure 6:
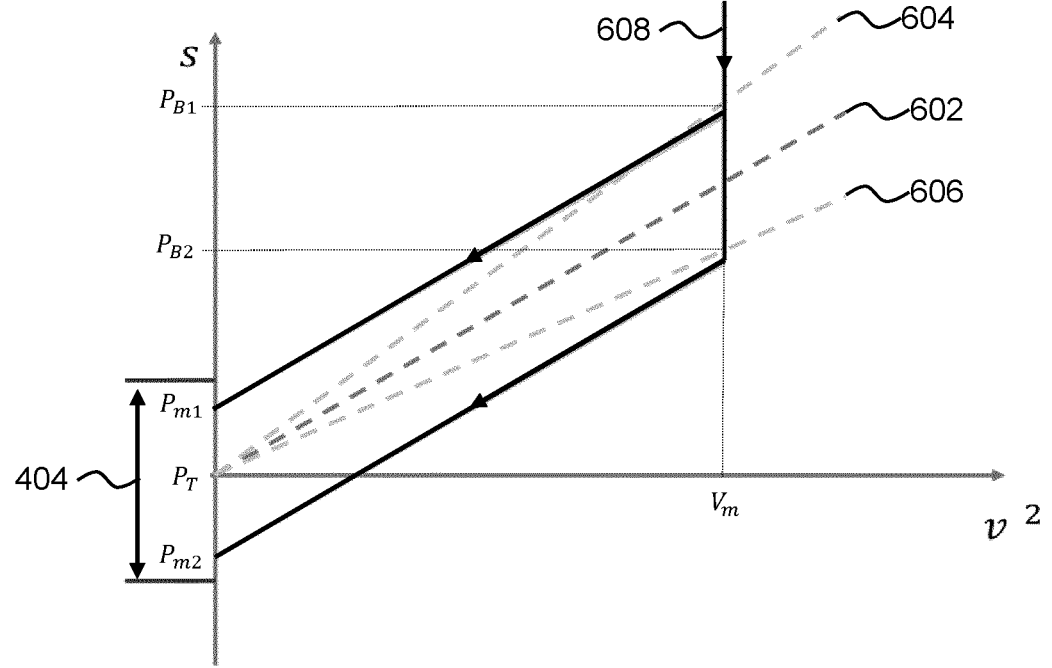
FIG. 6 shows an exemplary relationship between the braking distance S and the square of the measured velocity $V_m$.

FIG. 6 shows an exemplary relationship between the braking distance S and the square of the measured velocity $V_m$. A linear function between S and the square of $V_m$ may be used instead of the complex function according to equation (8) by assuming the constants b and c of equation 8 are negligible:

$$S = KV_m^2$$

The real value of the constant K is shown in line 602. The lines 604 and 606 show functions with alternate values of the constant K which are close to the real value of K. The thick line 608 shows the change in velocity of the component as the brake is applied for two different values of the constant K. When a function corresponding to line 604 is used as the braking function, the corresponding braking position is $P_{B1}$. As soon as the component reaches the braking position $P_{B1}$ the brake is enabled and the velocity of the component begins to drop with time. The rate at which the velocity begins to fall corresponds is based on the real value of K and thus the thick line 608 is parallel to the line 602 which corresponds to the real value of K. As the braking function used (corresponding to line 604) is not completely accurate, the position at which the component completely stops $P_{m1}$ will not be at the exact same position as the target position $P_T$. However, the measured position $P_{m1}$ does fall within the detent window 404 and thus there is no need to re-calibrate.

A similar situation occurs when a function corresponding to line 606 is used as the braking function. When the component reaches the braking position $P_{B2}$, the velocity begins to drop at a rate dictated by line 402 and stops at a position $P_{m2}$, which is slightly after the target position $P_T$. The measured position $P_{m2}$ is within the detent window 404 and thus no re-calibration would be needed.

Thus it is clear that the accuracy of the braking function may depend on the size of the detent window 404 which is chosen.

The skilled person would be readily capable of developing a processor for carrying out any herein described method. Thus, each step of a flow chart may represent a different action performed by a processor, and may be performed by a respective module of the processor.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A computer-implemented method for a medical imaging system, the method comprising:

obtaining a braking function between a distance moved by a moveable component of the medical imaging system when a brake is applied to the component and a velocity V of the component;

obtaining a measured velocity of the component before the brake is applied; and determining a braking position based on a target position, the measured velocity and the braking function, wherein the brake is configured to be actuated when the component reaches the braking position;

obtaining a measured position of the component after the component stops moving; and if a braking function re-calibration rule is triggered, adjusting the braking function based on:

a distance between the braking position and the measured position; and the measured velocity, wherein the braking function re-calibration rule includes that the measured position does not fall within a detent window relative to the target position.

2. The method of claim 1, wherein the braking function re-calibration rule further includes a rule of rejecting an accidental data.

3. The method of claim 1, wherein the braking function re-calibration rule further includes that the measured position fails to fall within the detent window relative to the target position.

4. The method of claim 1, wherein the braking function is a quadratic function between the distance moved by the component and the velocity of the component, wherein is a calibration constant and wherein adjusting the braking function comprises adjusting the value of the calibration constant.

5. The method of claim 1, wherein the braking function is a quadratic function between the distance moved by the component and the velocity of the component, wherein adjusting the braking function comprises adjusting the values of one or more of calibration constants.

6. The method of claim 1, wherein determining a braking position comprises:

determining a braking distance based on applying the measured velocity to the braking function; and determining the braking position based on the difference between the target position and the braking distance.

7. The method of claim 1, wherein obtaining the braking relationship comprises:

obtaining at least two measured distances travelled by the component when the brake is actuated;

obtaining at least two measured velocities corresponding to the velocity of the component when braking begins for the at least two measured distances respectively; and fitting a function for the at least two pairs.

8. A system for performing a detent method for a medical imaging system, the system comprising:

a memory that stores a plurality of instructions; and a processor coupled to the memory and configured to execute the plurality of instructions to:

obtain a braking function between a distance moved by a moveable component of the medical imaging system when a brake is applied to the component and a velocity of the component;

obtain a measured velocity of the component before the brake is applied; and determine a braking position based on a target position, the measured velocity and the braking function, wherein the brake is configured to be actuated when the component reaches the braking position;

obtain a measured position of the component after the component stops moving; and if a braking function re-calibration rule is triggered, adjust the braking function based on:

a distance between the braking position and the measured position; and the measured velocity;

wherein the braking function re-calibration rule includes that the measured position does not fall within a detent window relative to the target position.

9. The system of claim 8, wherein the braking function re-calibration rule includes a rule of rejecting an accidental data.

10. The system of claim 8, wherein the braking function re-calibration rule includes that the measured position fails to fall within the detent window relative to the target position.

11. The system of claim 8, wherein the braking function is a quadratic function between the distance moved by the component and the velocity of the component, wherein is a calibration constant and wherein the processor is configured to adjust the braking function by adjusting the value of the calibration constant.

12. The system of claim 8, wherein the braking function is a quadratic function between the distance moved by the component and the velocity of the component, wherein the processor is configured to adjust the braking function by adjusting the values of one or more of calibration constants.

13. The system of claim 8, further comprising:

one or more positioning rails;

the component placed on the positioning rails;

a movement system configured to move the component along the positioning rails; and a braking system configured to stop the component from moving.

14. The system of claim 8, further comprising one or more of:

a position sensor configured to obtain the measured position of the component; and a velocity sensor configured to determine the measured velocity of the component.

* * * * *